(12) United States Patent
Brushaber

(10) Patent No.: US 9,579,936 B2
(45) Date of Patent: Feb. 28, 2017

(54) TIRE DEFORMATION SENSOR AND TIRE INFLATION SYSTEM

(71) Applicant: Texas Research International, Inc., Austin, TX (US)

(72) Inventor: Robert Philip Brushaber, Austin, TX (US)

(73) Assignee: Texas Research International, Inc., Austin, TX (US)

( * ) Notice: Subject to any disclaimer, the term of this patent is extended or adjusted under 35 U.S.C. 154(b) by 0 days.

(21) Appl. No.: 14/438,877

(22) PCT Filed: Nov. 5, 2013

(86) PCT No.: PCT/US2013/068437
§ 371 (c)(1),
(2) Date: Apr. 27, 2015

(87) PCT Pub. No.: WO2014/074491
PCT Pub. Date: May 15, 2014

(65) Prior Publication Data
US 2015/0251502 A1  Sep. 10, 2015

Related U.S. Application Data

(60) Provisional application No. 61/723,296, filed on Nov. 6, 2012.

(51) Int. Cl.
| | | |
|---|---|---|
| *G01M 17/00* | (2006.01) | |
| *B60C 23/00* | (2006.01) | |
| *B60C 23/06* | (2006.01) | |
| *B60C 23/10* | (2006.01) | |
| *G01N 27/72* | (2006.01) | |

(52) U.S. Cl.
CPC .......... *B60C 23/004* (2013.01); *B60C 23/002* (2013.01); *B60C 23/066* (2013.01); *B60C 23/10* (2013.01); *G01N 27/72* (2013.01)

(58) Field of Classification Search
None
See application file for complete search history.

(56) References Cited

U.S. PATENT DOCUMENTS

| | | | |
|---|---|---|---|
| 6,518,877 B1 * | 2/2003 | Starkey | ................. B60C 23/004 |
| | | | 340/447 |
| 6,838,985 B2 | 1/2005 | Ghabra et al. | |
| 6,938,468 B1 | 9/2005 | Lin et al. | |
| 6,967,571 B2 | 11/2005 | Tsujita | |
| 7,019,630 B2 | 3/2006 | Katou | |
| 7,357,164 B2 | 4/2008 | Loewe | |
| 7,363,806 B2 | 4/2008 | Huang | |
| 7,487,671 B1 | 2/2009 | Zhu | |
| 7,603,894 B2 | 10/2009 | Breed | |
| 7,942,047 B2 | 5/2011 | Vassilieff et al. | |
| 8,044,783 B2 | 10/2011 | Ou et al. | |
| 8,240,198 B2 | 8/2012 | Schade et al. | |
| 2002/0166371 A1 | 11/2002 | Ratti et al. | |

(Continued)

*Primary Examiner* — Adam Alharbi
(74) *Attorney, Agent, or Firm* — Michael A. Ervin; M.A. Ervin & Associates LLC

(57) ABSTRACT

A tire deformation sensing and tire inflation system for a steel belted tires which makes use of magnetic coils embedded in the wheel assembly to detect the position of the tire's steel belting and uses the information obtained to adjust the tire pressure through a central tire inflation system.

10 Claims, 10 Drawing Sheets

(56) References Cited

U.S. PATENT DOCUMENTS

| | | |
|---|---|---|
| 2002/0190853 A1 | 12/2002 | Nigon |
| 2003/0010108 A1 | 1/2003 | Goslar et al. |
| 2005/0000278 A1 | 1/2005 | Haralampu et al. |
| 2006/0158802 A1 | 7/2006 | Kawashimo et al. |
| 2007/0151334 A1 | 7/2007 | Serra et al. |
| 2007/0295065 A1* | 12/2007 | Nordmeyer ............ B60G 11/15 73/117.03 |
| 2008/0216567 A1 | 9/2008 | Breed |
| 2010/0256874 A1 | 10/2010 | Carresjo et al. |
| 2012/0218095 A1 | 8/2012 | Zhou |

* cited by examiner

TIRE DEFORMATION SENSOR AND TIRE INFLATION SYSTEM

CROSS-REFERENCE TO RELATED APPLICATIONS

This application claims the benefit of U.S. Provisional application 61/723,296, filed on Nov. 6, 2012.

FIELD OF THE INVENTION

This disclosure relates generally to systems for continuously sensing the deformation of vehicle tires and adjusting the inflation of the tire based on those measurements.

BACKGROUND OF THE INVENTION

Off road vehicles, whether in the military or working trucks, must deal with highly variable soil conditions. Different soil conditions require different tire pressures to optimize traction. There are already Central Tire Inflation Systems (CTIS) that are being used to accurately vary the tire pressure while in the vehicle. However, the driver has top operate the system by using experience and or intuition.

Tire pressure, if adjusted properly, can lead to greater traction and efficiency. The proper pressure for a given tire is highly dependent on the given soil condition, and as soil conditions vary widely, the proper tire pressure can vary widely. For example, sandy and rocky conditions call for a relatively lowered tire pressure, whereas paved roads (which are a major part of the modern battlefield and used by millions of vehicles in the private sector) require a relatively higher tire pressure to ensure good efficiency. The US Army developed the Vehicle Cone Index (VCI) as a metric for directly quantifying the ability of vehicles to traverse soft-soil terrain. In order to ensure minimum soft-soil performance capabilities for their new military vehicles, the US Army has used VCI for many years as a performance specification. But readily measuring the VCI or any parameter that predicts the traction in a moving vehicle has been a long sought need.

There is a need then for a system that will detect when tire pressure is inappropriate or non-optimal and then adjust the tire pressure accordingly. The tire pressure detection can be based on the measurement of the static deflection of the tire. Such a detection system would enhance the capability of the vehicle when driving in harsh off-road conditions.

These needs can be met by the system to be disclosed, which makes use of magnetic coils embedded in the wheel assembly to detect the position of the tire's steel belting and uses the information obtained to adjust the tire pressure through a central tire inflation system.

BRIEF SUMMARY OF THE INVENTIVE CONCEPT

The needs described are met with a tire deformation sensing and tire inflation system for steel belted tires comprising: magnetic sensing coils embedded in the wheel assembly; a counterweight embedded in the wheel assembly on the opposite side from the magnetic coils; a power source for the magnetic coils; a central tire inflation system deployed in the tire; a data acquisition system to collect voltage signals from the magnetic sensing coils; software code to analyze collected data from data acquisition system; a central tire inflation system to adjust tire pressure based on instructions from the software code.

The needs are also met by a method for sensing tire deformation and inflating tires comprising the steps of: measuring an induced voltage signal from magnetic sensing coils embedded in the wheel assembly of the tire as the tire is turning; acquiring the induced voltage signal with a data acquisition system; transmitting the acquired induced voltage signal to software code that analyzes the information and sends instructions to a central tire inflation system; inflating or deflating the tire based on the instructions of the software code.

DETAILED DESCRIPTION OF THE INVENTION

In the following detailed description, reference is made to accompanying drawings that illustrate embodiments of the present invention. These embodiments are described in sufficient detail to enable a person of ordinary skill in the art to practice the invention without undue experimentation. It should be understood, however, that the embodiments and examples described herein are given by way of illustration only, and not by way of limitation. Various substitutions, modifications, additions, and rearrangements may be made without departing from the spirit of the present invention. Therefore, the description that follows is not to be taken in a limited sense, and the scope of the present invention is defined only by the appended claims.

Figure 1:
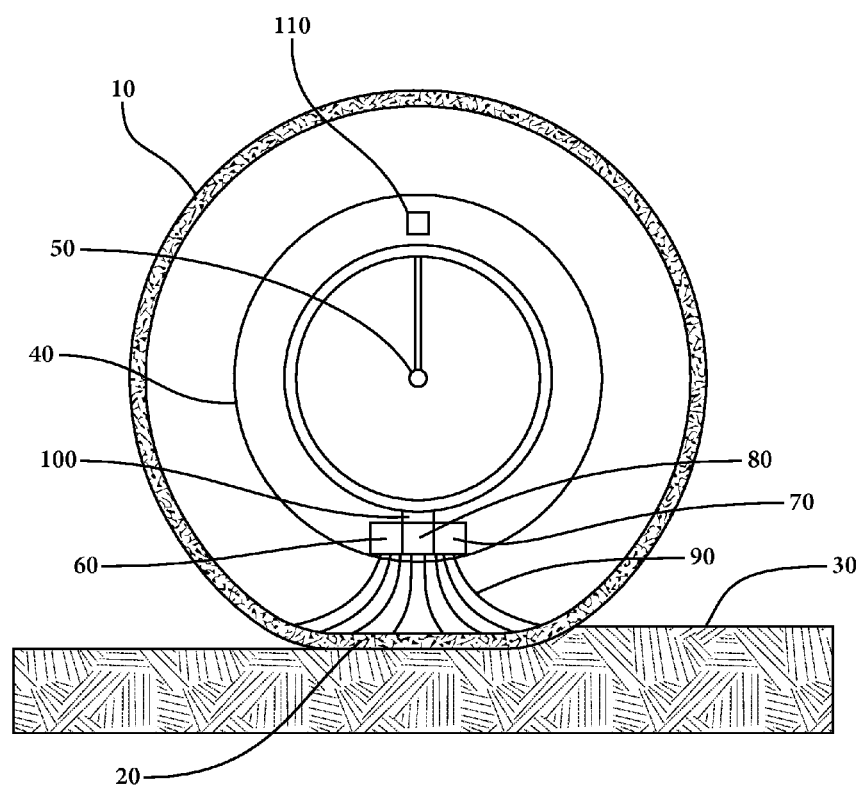
FIG. 1 illustrates a representative tire and the components of the proposed system of this disclosure.

FIG. 1 exhibits a representative tire and the components of the proposed system of this disclosure. The optimal type of tire deformation is a flat tire footprint. A sensing method is needed to detect the state of the tire tread (the type and amount of deformation) so that the pressure can be adjusted accordingly. A tire with a steel radial belt 10 is shown with a flat deformation on a representative surface 30. A run-flat 40 is shown on the tire interior. A run-flat is an interior portion of the tire that is designed to resist the effects of deflation when punctured, and to enable the vehicle to continue to be driven at reduced speeds and for limited distances. Shown in the center of the tire (without details) is a central tire inflation system (CTIS). The run flat 40 supports embedded magnetic coils that are used in this disclosure to detect the position and therefore the deformation of the tire's steel belting. Shown are left 60 and right 70 magnetic receiver coils on either side of one magnetic transmitter coil 80. The curved lines 90 represent the resulting magnetic flux. It should be noted that the proposed magnetic coils are not embedded in the tire itself but somewhere in the wheel assembly. In particular for many military tires this may be in the run flat.

Magnetic fields provide many opportunities for detecting tire deformation. The steel belts in radial belted tires present an especially convenient method of sensing deflection, since no modifications to the tire itself are necessary.

The magnetic coils can be a combination of one transmitter 80 and two receiver coils 60,70 as shown in FIG. 1. Alternately a single coil 85 with a tuned oscillator signal, shown in FIG. 2, could be used. The three-coil method of FIG. 1 would use two "receiver" coils 60, 70 positioned on either side of a "transmitter" coil 80. The "transmitter" coil will be energized with current, producing a time varying magnetic field. The magnetic field will induce voltage in the "receiver" coils. The induced voltage in the receiver coils will be monitored to detect the shape of the steel radial belts.

Figure 2:
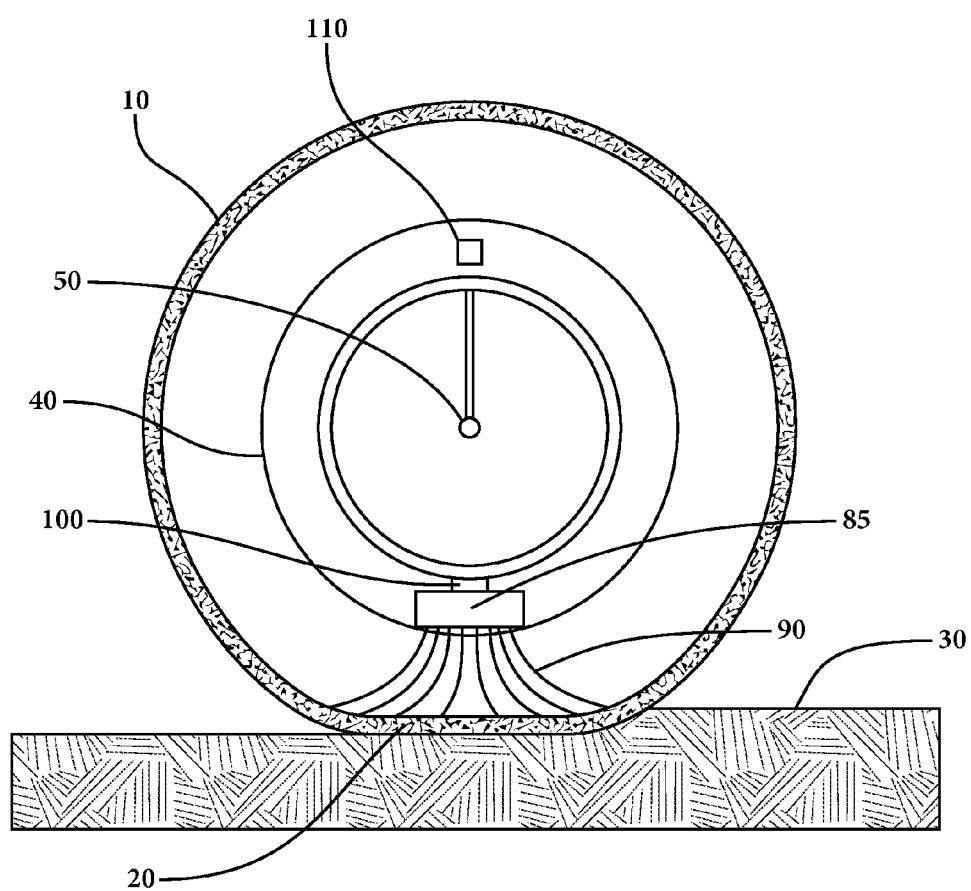
FIG. 2 illustrates an alternate embodiment of a representative tire and the components of the proposed system of this disclosure.

The single coil method shown in FIG. 2 would use a tuned oscillator and a capacitor 85 to produce a stable frequency. A second tunable internal oscillator would be tuned to the same frequency. Both frequencies' outputs would be mixed resulting in a beat frequency that would be equal to the difference between the frequencies. The distance between the coil and the steel radial belt will cause the coil oscillator to detune and change the beat frequency causing an output voltage that correlates to the shape of the steel radial belt.

Because of the weight added to one side of the wheel assembly by the magnetic coil system a counterweight 110 is placed on the opposite side of the wheel assembly.

To get power to the sensors, an energy harvester from the vibration and motion of the wheel would be optimal because everything would be contained inside the tire. A wireless transmitter and energy harvester 100 is shown. In another embodiment a slip ring (not shown) can be used to "hard wire" the needed power into the tire. This disclosure anticipates that either approach could be used.

The system as described in FIG. 1 is derived from the basic operation of a metal detector. The sensor is based on a three-coil design. This design uses amplitude modulated (AM) transmitting coil 80 and two receiving coils 60,70 on either side of the transmitter. The design and physical configuration of the receiving coils are instrumental in the ability to detect the shape of the steel radial belts in the tire. When there is a symmetric shape and amount of steel radial belts around the three-coil system, an equal but mirrored signal is produced on the two receiving coils. The resulting signals are summed together, effectively nullifying each other. When more metal is on one side of the three coils, a larger magnetic flux is pulled to that side of the coils and an induced voltage signal is given.

When the coils rotate toward the footprint of the tire, more magnetic field lines will pass through tire's footprint and the steel belts, increasing the flux through the path of the receiver coil closest to the steel belt. When the coils are directly above the footprint of the tire, the induced voltage in the receiver coils will be a reduced voltage because the magnetic field will be equal on both sides. As the coils begin to rotate past the footprint, the opposite receiver coil will have an induced voltage and then return to a reduced voltage after it passes the footprint. As the coils rotate inside the tire away from the footprint, there is reduced induced voltage in the receiver coil because the tire is round and the magnetic field is behaving the same on both sides of the transmitter coil.

Figure 3:
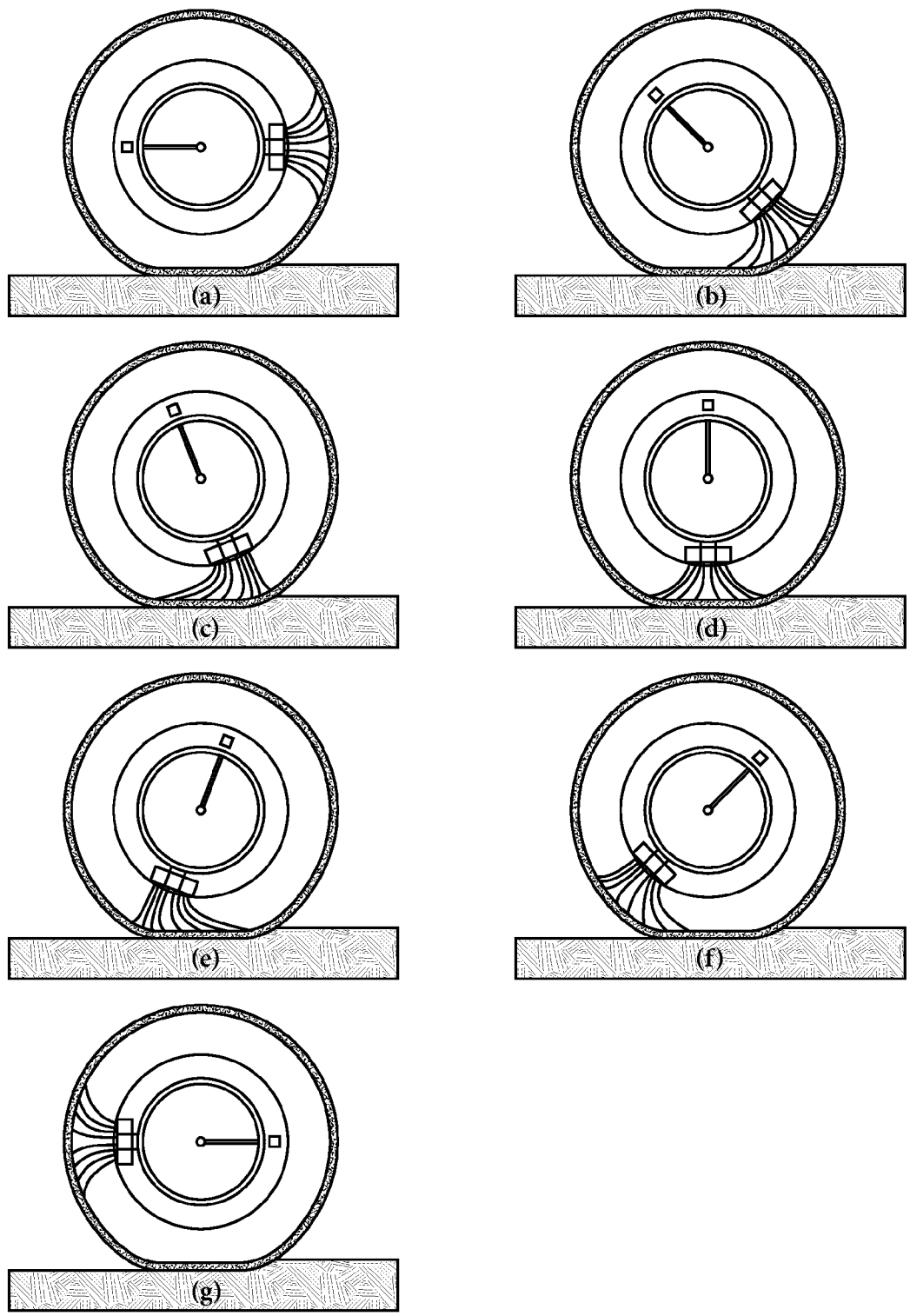
FIG. 3 is a series of tire rotation positions illustrating the changes in the magnetic flux from the proposed system of FIG. 1.

Turning now to FIG. 3, the tire using the three-coil system is shown rotating through a 180-degree cycle. At step (a), where the coils are well away from the footprint the induced voltage will be a reduced voltage. As the magnetic sensors rotate toward the tire footprint (b) and (c), the change in the shape of the steel radial belt will induce a voltage in the receiver coils because of the imbalance of the magnetic flux due to the receiver being closer to the steel radial belt in the tire footprint. The induced voltage returns to a reduced voltage as the sensor rotates to directly above the footprint (d) because the magnetic flux is balanced. When the coils reach the other side of the footprint (e) and (f) the voltage is induced again, then returns to a reduced voltage at (g).

Figure 4:
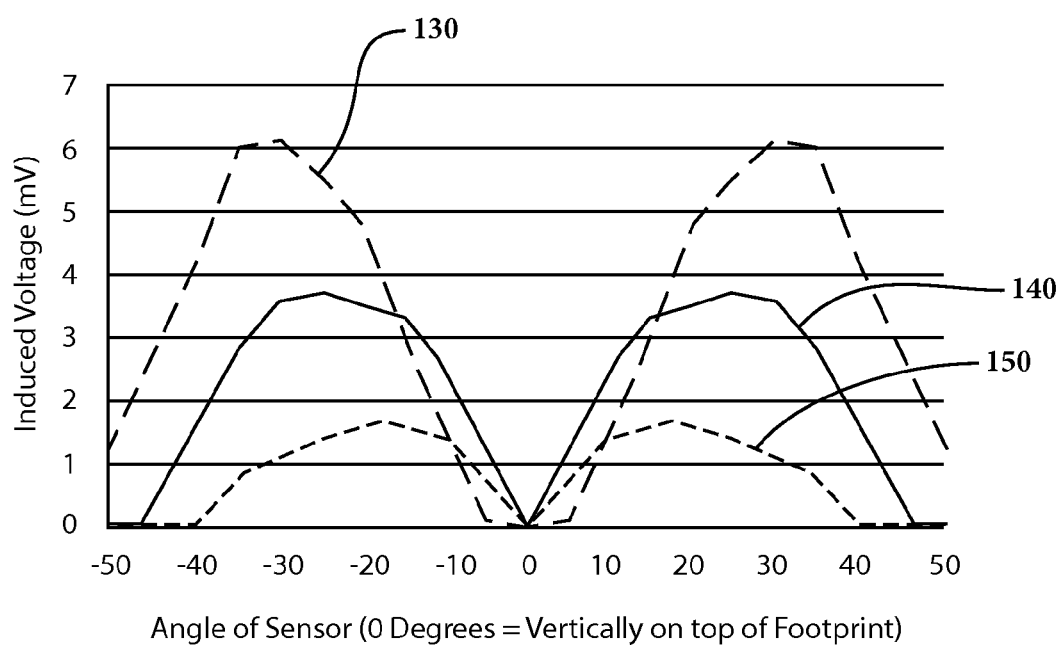
FIG. 4 illustrates some typical induced voltage data from the system of FIG. 1.

Recognizing that the exact results will vary with different tires—FIG. 4 shows a typical induced voltage graph from an experimental tire that has been tested in the states of under 130, optimal 140, and over 150 inflation.

The distance between the two peaks correlates to the length of the tire footprint. The slope of the lines correlates to the flatness of the footprint. Repeated testing of different tires can be used to find the optimal tire footprint to achieve the optimal (lowest) Vehicle Cone Index (VCI).

The induced voltage amplitude directly correlates to the distance between the radial belts and the coils; the larger the amplitude, the closer the belts. The sensor rotation angles between the peak voltages are related to the length of the footprint; the higher the sensor rotation angles and peak voltage, the longer the footprint. The voltage will go to a reduced voltage when it is straight up and down (at zero degrees) because the same amount of flux will pass through both receiver coils. The slope of the induced voltage curve will either increase or decrease depending upon whether the tire is deflected inward, outward, or flat. By knowing these parameters, it is possible to determine both the distance to the radial belts and the size of the footprint.

Results from testing the a single coil 85 with a tuned oscillator signal, of FIG. 2 are shown in FIGS. 5, 6, 7, and 8. As the distance between a tires coil and the steel radial belt changes it will cause the coil oscillator to detune and change the beat frequency causing an output DC voltage that correlates to the shape of the steel radial belt.

The electronics of the single coil system allowed the setting of the sensitivity and the discrimination of the single coil with tuned oscillator combination. It was found that the results ranged from 1600 mv to 3500 mv at every combination of settings. The different deflection levels were very repeatable and were sensitive. This approach gave the largest swing in the mv voltage.

Figure 5:
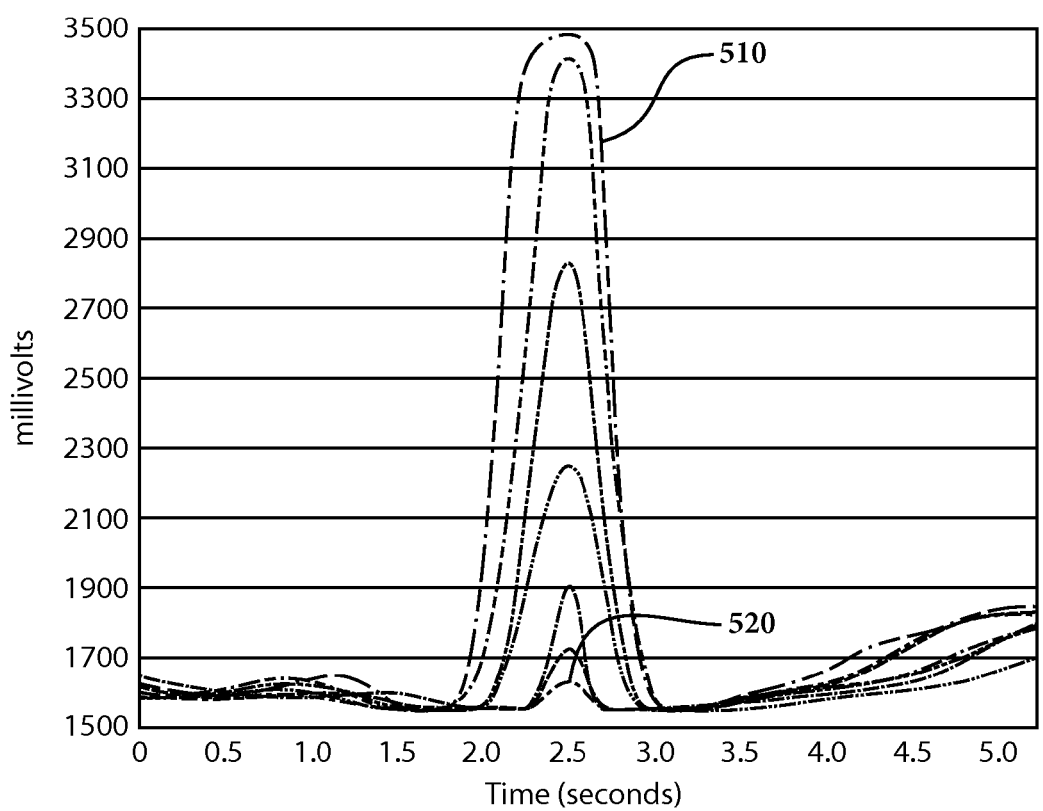
FIG. 5 illustrates the experimental data of the results with the oscillator coil of FIG. 2 set to maximum sensitivity and maximum discrimination.

FIG. 5 shows the results with the oscillator coil set to maximum sensitivity and maximum discrimination. The deflection levels ran from a maximum 510 (most deflection) of about 3495 mv to a minimum 520 (least deflection) of about 1610 mv.

Figure 6:
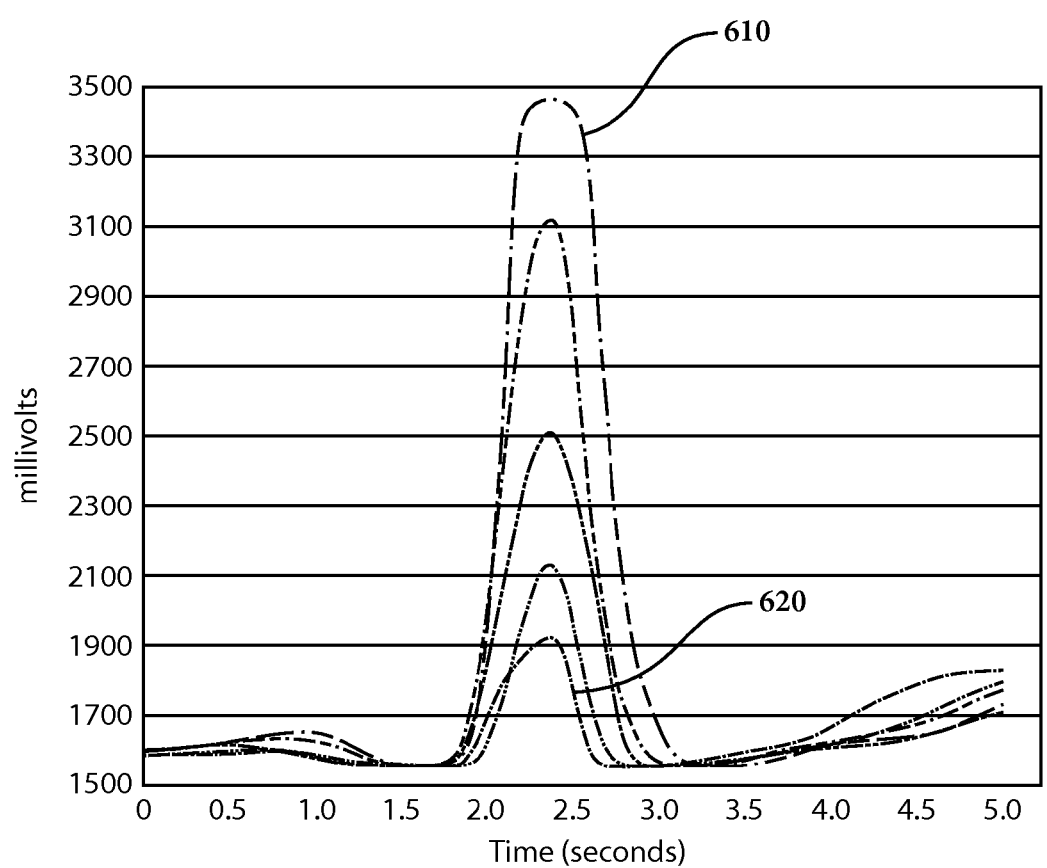
FIG. 6 illustrates the experimental data of the results with the oscillator coil of FIG. 2 set to half sensitivity and maximum discrimination.

FIG. 6 shows the results with the oscillator coil set to half sensitivity and maximum discrimination. The deflection levels ran from a maximum 610 (most deflection) of about 3475 mv to a minimum 620 (least deflection) of about 1905 mv.

Figure 7:
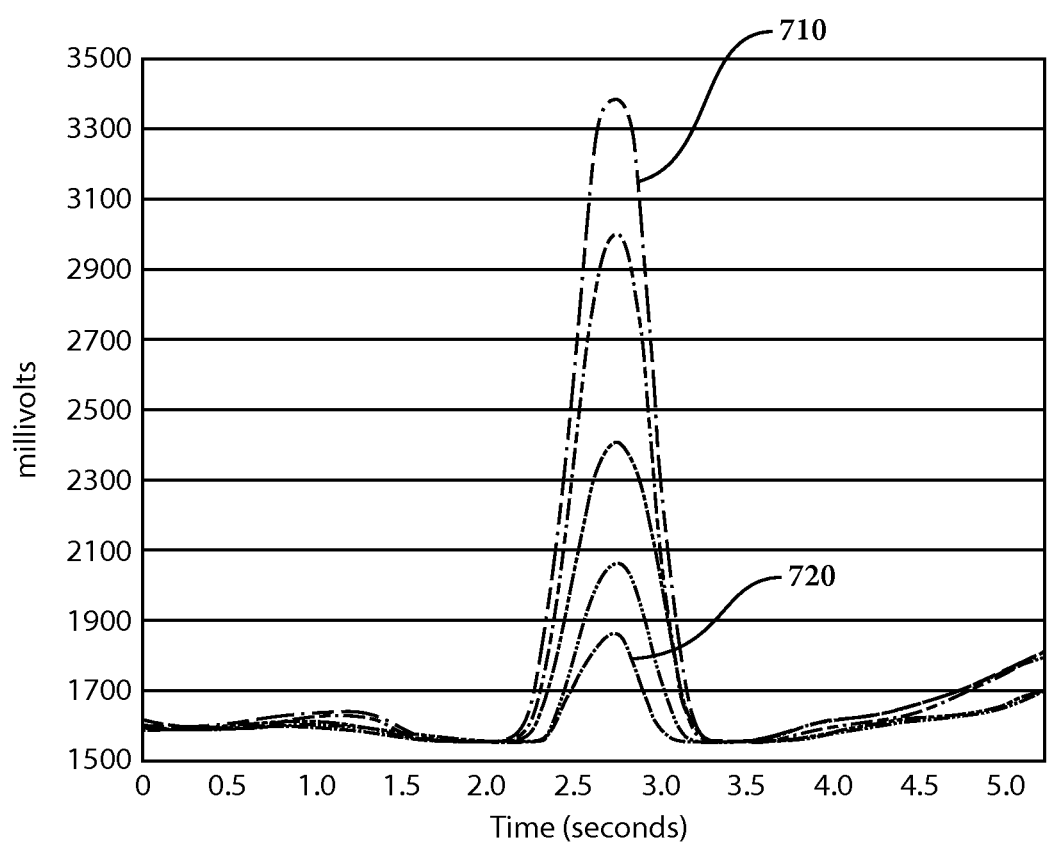
FIG. 7 illustrates the experimental data of the results with the oscillator coil of FIG. 2 set to minimum sensitivity and maximum discrimination.

FIG. 7 shows the results with the oscillator coil set to minimum sensitivity and maximum discrimination. The deflection levels ran from a maximum 710 (most deflection) of about 3380 mv to a minimum 720 (least deflection) of about 1860 mv.

Figure 8:
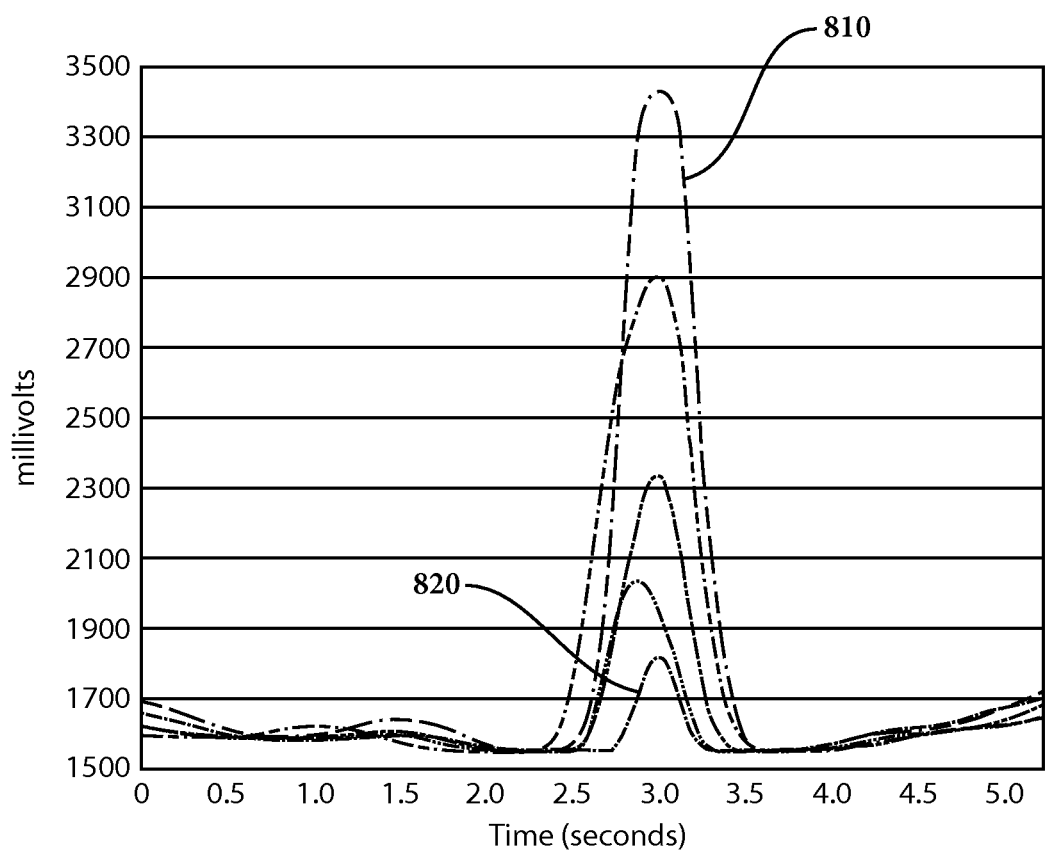
FIG. 8 illustrates the experimental data of the results with the oscillator coil of FIG. 2 set to minimum sensitivity and minimum discrimination.

FIG. 8 shows the results with the oscillator coil set to minimum sensitivity and minimum discrimination. The deflection levels ran from a maximum 810 (most deflection) of about 3420 mv to a minimum 820 (least deflection) of about 1810 mv.

Figure 9:
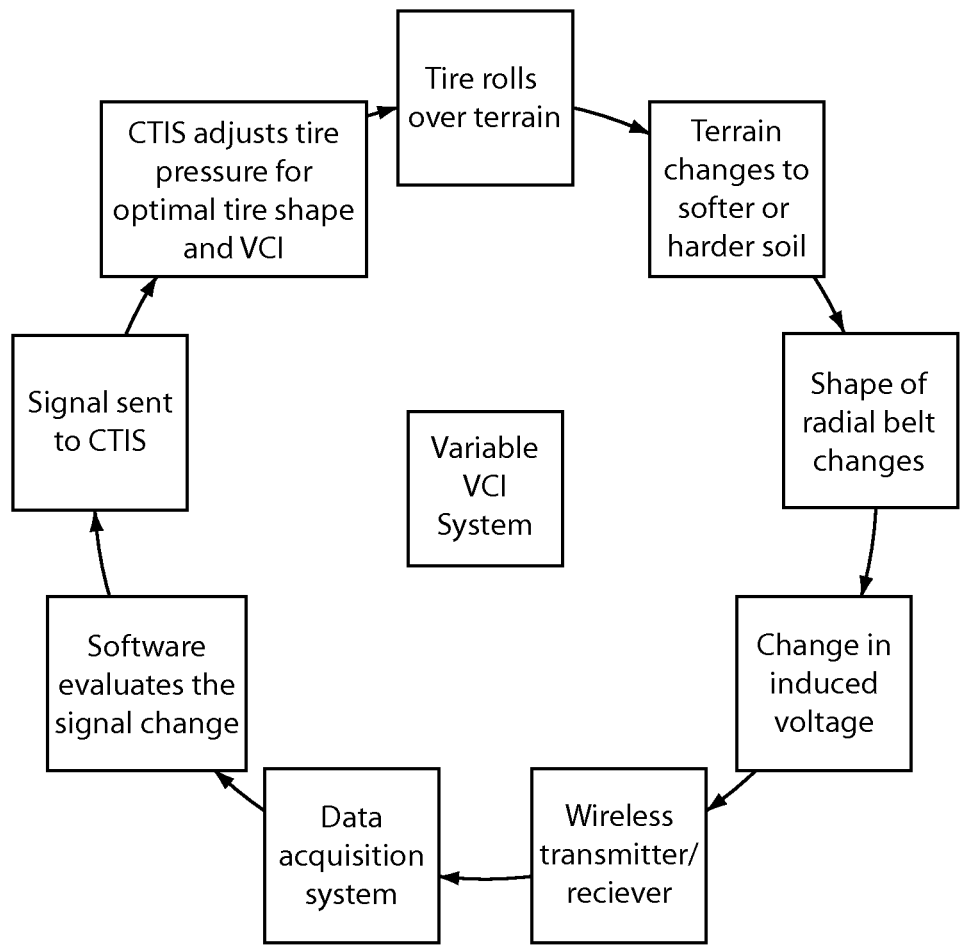
FIG. 9 is an operation flowchart of the tire deformation and inflation system of this disclosure.

The operation (method) of the complete system is shown in FIG. 9. The cycle begins at the top of the Figure with the tire rolling over the terrain and proceeds clockwise around the circle ends with the CTIS adjusting the tire pressure for optimal tire shape and VCI.

Figure 10:
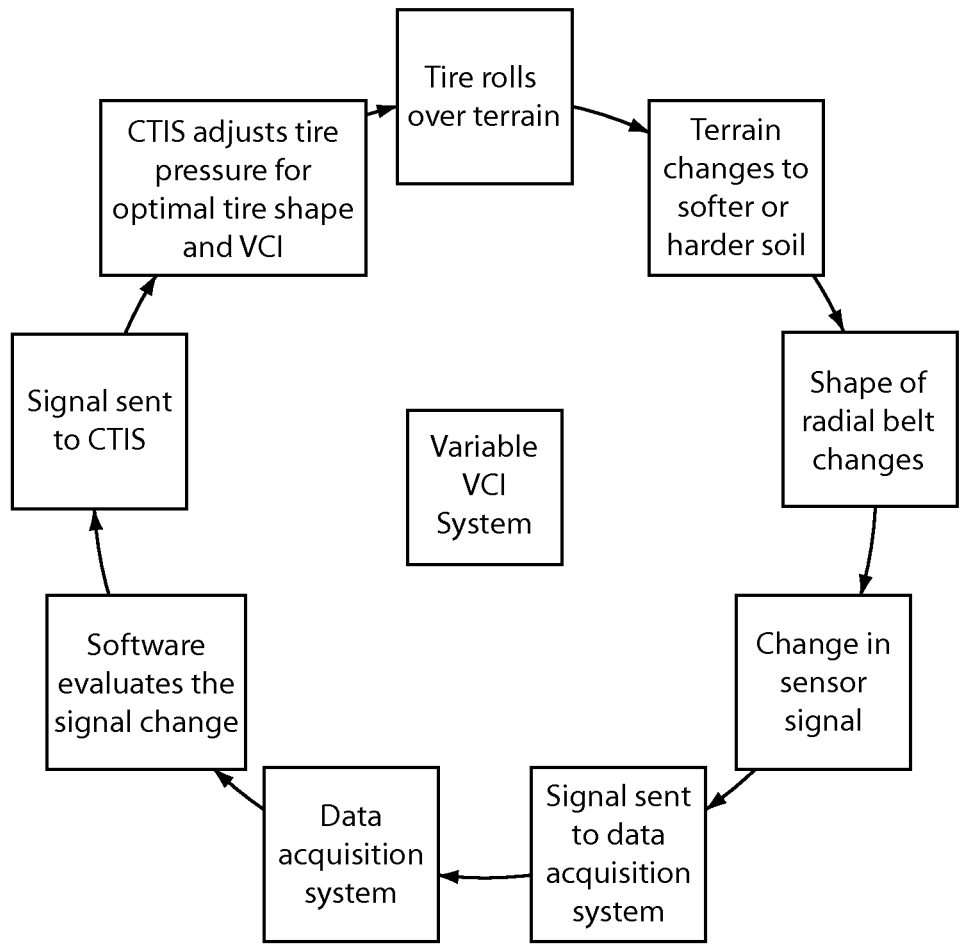
FIG. 10 is an alternate embodiment of the tire deformation and inflation system of this disclosure.

In another embodiment (different than FIG. 9), the wireless system is replaced by a hardwired system, as shown in FIG. 10.

The overall system, which may be called the Variable VCI System includes the following components:

1. A power source or a scavenging/recharging system.
2. The tire deformation sensors (three-coil or tuned oscillator).
3. Signal Processor/digitizing.
4. A wireless transmitter.
5. A wireless receiver (or alternately a wired power source).
6. The software (tells the CTIS when and how much to adjust pressure).
7. An interface with the CTIS.

The magnetic sensors described could easily last the lifetime of the vehicle, if corrosion is prevented by encapsulating the coils in the run flat or polyurethane. Since there are no moving parts, vibration and acceleration will not pose a problem. Since the coils are evenly distributed around the wheel, imbalance will be small and determined by the tolerances of the run-flat insert. The materials necessary are relatively inexpensive, especially in bulk. The magnetic sensor will also withstand high temperatures; though temperature may affect the response of the device, temperature compensation can be made. The device has the opportunity for good resolution if properly tuned and manufactured with tight tolerance. The information is, however, only one-dimensional; therefore, the shape of the tire cannot be determined from the signal. Fortunately, it is not necessary to know the exact shape of the tire to determine an appropriate tire pressure for the terrain. Also, the magnetic sensor has the benefit of no moving parts and no maintenance.

Power Embodiments

The primary problem in any rotational system is to get power to the devices being used within. As previously discussed power for the magnetic sensors can be supplied through a power harvesting system using the kinetic energy from the movement of the wheel. Alternately it can be supplied through a slip ring on the wheel.

Considering the wheel is rotating and bouncing almost constantly makes power harvesting an excellent candidate for this application. Piezo-transformers or embedded magnets could generate several Watts of power in a wheel hub, enough to drive the sensing electronics and the wireless module as suggested above. Typically, the technology is almost commercially available today and consists of a pre-stressed and loaded piezo-beam which translates the vibrational energy into a high voltage that is converted to a low voltage high current output power source. The tire sensor electronics and wireless modules can be optimized for very low power operation thus making the entire sensor unit modular, robust, permanent, self-sustaining and independent of the vehicle electrical systems.

Because some military applications prohibit the use of wireless transmission the other embodiment for power is a slip ring. A slip ring is a method of making an electrical connection through a rotating assembly. Slip rings are also called rotary electrical interfaces, rotating electrical connectors, swivels, or electrical rotary joints. This disclosure anticipates any such connection. In a slip ring either the brushes or the rings are stationary and the other component rotates. Some slip rings use mercury wetted slip rings, noted for their low resistance and stable connection by replacing a sliding brush contact with a pool of liquid metal molecularly bonded to the contacts. This disclosure anticipates any of these slip ring embodiments.

Magnetic Coil Embodiments

One option, already shown in FIG. 1, is to have the magnetic coils as a combination of transmitter and receiver coils. The "receiver" coils would be positioned on either side of a "transmitter" coil. The "transmitter" coil will be energized with current, producing a time varying magnetic field. The magnetic field will induce voltage in the "receiver" coils when there is an imbalance of metal to one side. The induced voltage in the receiver coils will be monitored to detect the shape of the steel radial belts.

Another method illustrated in FIG. 2 is used in metal detectors and is essentially a coil of wire that is part of a tuned oscillator (i.e. an electronic oscillator that uses an inductor (i.e. the coil)) and a capacitor to produce a very stable oscillation frequency. The unit also contains a local tunable internal oscillator that can be tuned to the same frequency. Both these frequency outputs are "mixed" resulting in a "beat" frequency that is equal to the difference between them. This is converted to a DC signal. In operation, the internal oscillator is tuned such that the beat frequency is reduced voltage or very low. The proximity of the "search" coil to a piece of metal causes the coil oscillator to "detune" or change in frequency resulting in a difference in the beat frequency, causing the output of the unit to change the DC output voltage. The advantage of this system is that it uses only one coil. This disclosure anticipates either of these magnetic coil embodiments.

Although certain embodiments of the present invention and their advantages have been described herein in detail, it should be understood that various changes, substitutions and alterations can be made without departing from the spirit and scope of the invention as defined by the appended claims. Moreover, the scope of the present invention is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufactures, means, methods or steps.

I claim:

1. A tire deformation sensing and tire inflation system for a steel belted tire comprising:
   a. At least one magnetic sensing coil embedded in the wheel assembly, wherein the at least one magnetic sensing coil embedded in the wheel assembly comprises a three coil system with two receiver coils positioned on opposite sides of a transmitter coil;

b. a counterweight embedded in the wheel assembly on the opposite side from said magnetic coils;
c. a power source for said magnetic coils;
d. a central tire inflation system deployed in the tire;
e. a data acquisition system to collect voltage signals from said magnetic sensing coils;
f. software code to analyze collected data from data acquisition system;
g. a central tire inflation system to adjust tire pressure based on instructions from said software code.

2. The tire deformation sensing and tire inflation system for a steel belted tire of claim 1 wherein the at least one magnetic sensing coil embedded in the wheel assembly comprises a single coil of wire that is part of a tuned oscillator.

3. The tire deformation sensing and tire inflation system for a steel belted tire of claim 1 wherein the power source for the system is supplied through a power harvesting system using the kinetic energy from the movement of the wheel.

4. The tire deformation sensing and tire inflation system for a steel belted tire of claim 3 wherein the power harvesting system using the kinetic energy from the movement of the wheel utilizes Piezo-transformers and/or embedded magnets to harvest the power.

5. The tire deformation sensing and tire inflation system for a steel belted tire of claim 1 wherein the power source for the system is supplied via a slip ring.

6. A method for sensing tire deformation and inflating a tire comprising the steps of:

a. measuring an induced voltage signal from at least one magnetic sensing coil embedded in the wheel assembly of the tire as the tire is turning, wherein the at least one magnetic sensing coil embedded in the wheel assembly comprises a three coil system with two receiver coils positioned on opposite sides of a transmitter coil,
b. acquiring the induced voltage signal with a data acquisition system;
c. transmitting the acquired induced voltage signal to software code that analyzes the information and sends instructions to a central tire inflation system; and
d. inflating or deflating the tire based on the instructions of the software code.

7. The method of sensing tire deformation and inflating a tire of claim 6 wherein the at least one magnetic sensing coil embedded in the wheel assembly comprises a single coil of wire that is part of a tuned oscillator.

8. The method of sensing tire deformation and inflating a tire of claim 6 wherein the power source for the system is supplied through a power harvesting system using the kinetic energy from the movement of the wheel.

9. The method of sensing tire deformation and inflating a tire of claim 6 wherein the power harvesting system using the kinetic energy from the movement of the wheel utilizes Piezo-transformers and/or embedded magnets to harvest the power.

10. The method of sensing tire deformation and inflating a tire of claim 6 wherein the power source for the system is supplied via a slip ring.

* * * * *